United States Patent [19]

Clubley et al.

[11] Patent Number: 4,656,200

[45] Date of Patent: Apr. 7, 1987

[54] PHOSPHONIC ACID SALTS AS FLAME RETARDANTS FOR POLYURETHANES AND POLYISOCYANURATES

[75] Inventors: Brian G. Clubley, Wilmslow; Richard J. Dellar, Altrincham; David L. Buszard, Woodford; Norman Richardson, Middleton, all of England

[73] Assignee: Ciba-Geigy AG, Basel, Switzerland

[21] Appl. No.: 691,311

[22] Filed: Jan. 14, 1985

[30] Foreign Application Priority Data

Jan. 14, 1984 [GB] United Kingdom ................ 8401003
Mar. 20, 1984 [GB] United Kingdom ................ 8407226
Jul. 9, 1984 [GB] United Kingdom ................ 8417462
Aug. 3, 1984 [GB] United Kingdom ................ 8419791

[51] Int. Cl.$^4$ ........................ C08G 18/14; C08K 5/53
[52] U.S. Cl. .................................. 521/108; 524/130; 524/132; 521/902; 528/51; 260/502.4 R; 260/501.21; 260/501.15; 558/207; 546/304; 546/347

[58] Field of Search ................ 521/108, 902; 528/51; 524/130, 132

[56] References Cited

U.S. PATENT DOCUMENTS

| 4,264,516 | 4/1981 | Hiestand | 260/404.5 |
| 4,430,453 | 2/1984 | Seifert et al. | 521/108 |
| 4,452,849 | 6/1984 | Nachbur et al. | 428/264 |
| 4,487,800 | 12/1984 | Nachbur et al. | 428/265 |

FOREIGN PATENT DOCUMENTS 0012106 6/1980 European Pat. Off.
1324691 7/1973 United Kingdom.

Primary Examiner—Herbert S. Cockeram
Attorney, Agent, or Firm—Wenderoth, Lind & Ponack

[57] ABSTRACT

The invention provides salts of methyl phosphonic acid and its mono- or di-methyl ester with certain amines. The salts are useful flame retardant additives for polyurethanes and polyisocyanurates.

1 Claim, No Drawings

PHOSPHONIC ACID SALTS AS FLAME RETARDANTS FOR POLYURETHANES AND POLYISOCYANURATES

The present invention relates to amine salts of phosphonic acids and their use in rendering polyurethanes and polyisocyanurates more flame retardant.

Polyurethanes and polyisocyanurates are usually made more flame retardant by adding a phosphorus-containing compound, a halogen-containing compound or a mixture thereof. One commonly used phosphorus-containing compound is dimethylmethylphosphonate (DMMP). However there are certain problems associated with the use of DMMP. First it is a relatively volatile liquid (boiling point 181° C.) which means that material may be lost by volatilisation under certain circumstances. Secondly, DMMP is usually formulated with polyols used to manufacture polyurethanes and polyisocyanurates together with catalysts, blowing agents and other ingredients, before the isocyanate is added. There is a tendency for the formulation to be somewhat unstable if it is stored for a long period before use. The viscosity of such formulations may increase on standing and variable foaming characteristics may be observed when mixed with the isocyanate co-reactant.

Ethanolamine salts of methylphosphonic acid and their use as additives for hydraulic fluids are disclosed in European Patent Application No. 0 012 106.

It is an object of the present invention to provide novel phosphorus-containing flame retardants of low volatility and which give polyol formulations which are stable on storage.

Accordingly the present invention provides amine salts of phosphonic acids of the general formula Ia and/or Ib

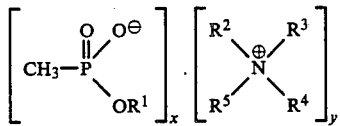

(Ia)

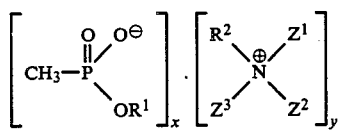

(Ib)

wherein x and y are integers such that the number of negative and positive charges are the same, $R^1$ is hydrogen, methyl or a negative charge $R^2$ is hydrogen or methyl, $R^3$ is a $C_2$–$C_4$ alkyl group substituted by 1–3 hydroxyl groups, which may be substituted by an oxyalkylene chain, these being not more than one hydroxyl group on any one carbon atom, $R^4$ and $R^5$ may be the same or different and may be a group as defined for $R^3$, or hydrogen, a $C_1$–$C_4$ alkyl group, a phenyl group, a benzyl group, or a phenyl or benzyl group substituted on the aromatic ring by an alkyl group of 1–12 carbon atoms, a hydroxyl group, which may be substituted by an oxyalkylene chain, and/or 1–3 halogen atoms, or $R^5$ is a group of the formula II

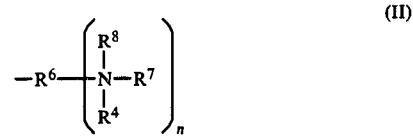

(II)

wherein $R^6$ is an alkylene group of 2–4 carbon atoms, a phenylene group, a xylylene group, a diphenyl group or is a group of the formula

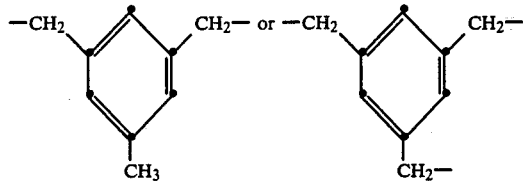

in which aromatic rings in a group $R^6$ may be substituted by an alkyl group of 1–12 carbon atoms, a hydroxyl group, which may be substituted by an oxyalkylene chain, and/or 1–3 halogen atoms, and $R^7$ is hydrogen or methyl, in which cases the nitrogen atom carries a positive charge, or $R^7$ is absent; $R^8$ is hydrogen or a group as defined for $R^3$ and n is 1 or 2;

or $R^4$ and $R^5$ may be joined to form, with the nitrogen, 5 or 6 membered heterocyclic ring, optionally containing an oxygen atom; and $Z^1$, $Z^2$ and $Z^3$ are the same or different and represent hydrogen, a $C_1$–$C_{12}$ straight or branched chain alkyl group, a $C_3$–$C_{12}$ straight or branched chain alkenyl group, a $C_3$–$C_{12}$ straight or branched chain alkynyl group, a $C_4$–$C_{12}$ cycloalkyl group, a phenyl or naphthyl group which may be substituted by a $C_1$–$C_4$ straight or branched chain alkyl group, a $C_1$–$C_4$ alkoxy group, amino, methylamino, halogen or nitro, or a $C_7$–$C_{12}$ aralkyl group;

or $Z^2$ or $Z^3$ together with the nitrogen atom to which they are attached form a saturated or unsaturated 3–7 membered ring system which may optionally contain another hetero atom, and the ring system is optionally substituted by a $C_1$–$C_4$ straight or branched chain alkyl group, a $C_1$–$C_4$ alkoxy group, amino, methylamino, a $C_1$–$C_4$ aminoalkyl group, halogen or nitro;

or $Z^1$, $Z^2$ and $Z^3$ together with the nitrogen atom to which they are attached form an 8–12 membered bicyclic ring optionally containing another hetero atom, or $Z^1$ is a group of the formula

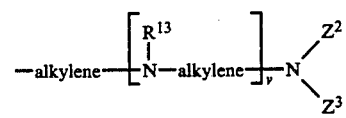

wherein alkylene is a group containing 2 to 12 carbon atoms, v is 0 or an integer from 1 to 5, $R^{13}$ is hydrogen or a $C_1$–$C_{16}$ straight or branched chain alkyl group, and $Z^2$ and $Z^3$ are as defined above;

or $Z^1$ is a group of the formula

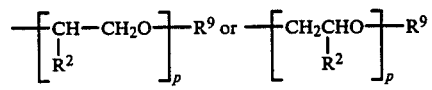

in which $R^2$ is as defined above, $R^9$ is a $C_1$-$C_{12}$ alkyl group and p is an integer from 1-10, preferably from 1-4;

or $Z^3$ is a group of the formula IIa

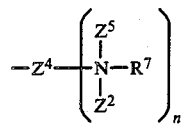
(IIa)

wherein $Z^4$ is an alkylene group of 2-12 carbon atoms, a phenylene group, a xylylene group, a diphenyl methane group or a group of the formula

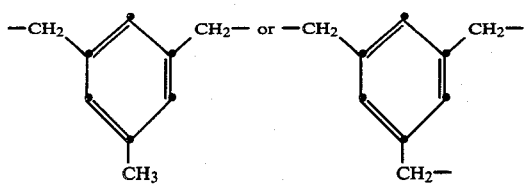

in which aromatic rings in a group $Z^4$ may be substituted by an alkyl group of 1-12 carbon atoms, hydroxyl and/or 1-3 halogen atoms, and $R^7$ is hydrogen or methyl, in which cases the nitrogen atom carries a positive charge, or $R^7$ is absent; $Z^5$ is hydrogen or a group as defined for $Z^1$ and n is 1 or 2; or $Z^2$ and $Z^5$ may be joined to form, with the nitrogen, a 3 to 7 membered heterocyclic ring, optionally containing another hetero atom;

provided that (a) when the salt of the formula Ib is absent and $R^1$ is hydrogen or a negative charge and $R^2$ is hydrogen at least one of $R^3$, $R^4$ and $R^5$ is other than hydrogen or a β-hydroxyethyl group, and further provided.

that (b) when the salt of the formula Ia is absent and $R^1$ is hydrogen or a negative charge, $R^2$ is hydrogen and two of the radicals $Z^1$, $Z^2$ and $Z^3$ are hydrogen the other one is not alkyl or alkenyl having more than 7 carbon atoms.

When hydroxyl groups in $R^3$, $R^4$ and $R^5$ are substituted by an oxyalkylene chain, the chain may have the formula

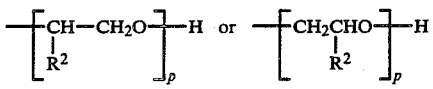

in which $R^2$ is as defined above and p is an integer from 1-10, preferably from 1-4.

When $R^3$, $R^4$ or $R^5$ is a $C_2$-$C_4$ alkyl group substituted by 1 to 3 hydroxyl groups, it may be, for example, 2-hydroxyethyl, 2-hydroxy-n-propyl or trimethylolmethyl.

When $R^4$ or $R^5$ is a $C_1$-$C_4$ alkyl group, it may be, for example, methyl, ethyl, isopropyl, n-butyl or sec-butyl.

When $R^4$ or $R^5$ is a phenyl or benzyl group substituted on the aromatic ring by an alkyl group of 1-12 carbon atoms, this alkyl group may be, for example, methyl, ethyl, isopropyl, n-butyl, t-butyl, n-hexyl, n-octyl, n-nonyl or octadecyl.

Further non-limiting examples of $R^3$, $R^4$ and $R^5$ are given in the list of amines of formula IV which may be used for the preparation of the salts of formula Ia.

$Z^1$, $Z^2$ and $Z^3$ may have the following significance:

$C_1$-$C_{12}$ alkyl groups include methyl, ethyl, isopropyl, n-butyl, sec-butyl, octyl and dodecyl;

$C_3$-$C_{12}$ alkenyl groups include allyl, propenyl, butenyl, hexenyl, dodecenyl;

$C_3$-$C_{12}$ alkynyl groups include propargyl;

$C_4$-$C_{12}$ cycloalkyl groups include cyclobutyl, cyclopentyl, cyclohexyl, cyclooctyl and cyclododecyl;

aralkyl groups include benzyl, phenethyl and 1-naphthylmethyl;

optionally substituted aryl groups include phenyl, methoxyphenyl, aminophenyl, nitrophenyl, chlorophenyl and naphthyl; aminoalkyl groups include aminoethyl and aminopropyl.

When $Z^2$ and $Z^3$ together with the nitrogen atom to which they are attached form a 3-7 membered ring system, it may be, for example, pyridino, morpholino, piperidino, piperazino, 2-aminopyridino, 2-methoxypyridino or 3-chloropyridino.

Further non-limiting examples of $Z^1$, $Z^2$ and $Z^3$ are given in the list of amines of formula V which may be used for the preparation of the salts of formula Ib.

Amine salts of formula Ia are preferred:

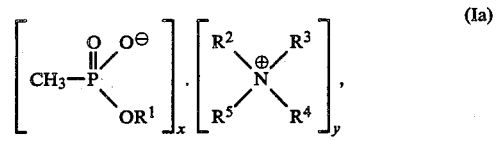
(Ia)

wherein x, y, $R^1$, $R^2$, $R^3$, $R^4$ and $R^5$ are as defined above.

Further, amine salts of formula Ib are also preferred:

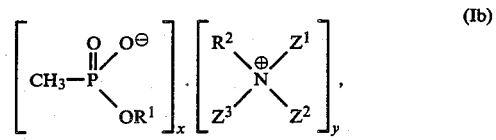
(Ib)

wherein x, y, $R^1$, $R^2$, $Z^1$, $Z^2$ and $Z^3$ are as defined above. $R^1$ is preferably methyl.

In the formula Ia, $R^2$ is preferably methyl and $R^3$ and $R^4$ are preferably hydroxyethyl.

In the formulae Ia and Ib, $R^1$ and $R^2$ are preferably methyl.

The amine salts of the invention may be prepared by reacting methylphosphonic acid or ester of the formula III

(III)

wherein $R^2$ is defined above and $R^{10}$ is hydrogen or methyl, with an amine of the formula IV and/or V

(VI)

(V)

wherein $R^3$, $R^4$, $R^5$, $Z^1$, $Z^2$ and $Z^3$ are as defined above, optionally in an aqueous or organic solvent and optionally under an inert gas atmosphere, and heating if necessary to cause the salt to form.

The amount of methylphosphonic acid or ester of formula III is that which will react with one or more of the amine groups in the amine of formula IV or V to give a mono-salt, di-salt or higher salt as desired.

If methylphosphonic acid or its monomethyl ester is used, formation of the salt is rapid and mild conditions may be used. The acid and amine may be simply mixed at room temperature to form the salt.

If the amine is a viscous liquid or solid, the mixture may be heated, e.g. up to 100° C. to ensure efficient reaction. If desired an aqueous or organic solvent may be used and is removed at the end of the reaction.

If DMMP is used more vigorous reaction conditions are needed to ensure salt formation. The DMMP/amine mixture may be heated up to 180° C., optionally under an inert gas such as nitrogen. Heating at 100° C. to 180° C. for several hours may be needed. If desired the reaction may be performed in an organic solvent, for example a hydrocarbon solvent such as toluene or xylene.

The methylphosphonic acid and its esters and the amines used in the present invention are all known compounds and may be prepared in known ways.

When products are made which contain oxyalkylene chains, these may be incorporated either by reacting the amine with an alkylene oxide, followed by salt formation, or the amine is reacted to form the salt which is then reacted with an alkylene oxide. Etherification can be carried out as desired before or after salt formation. From 1 to 10 moles of ethylene oxide and/or propylene oxide per mole of amine or salt may be used. The alkoxylation may be carried out at a temperature of 30° C. to 200° C., in the presence or absence of a catalyst.

Amines of formula IV containing oxyalkylene chains which may be used in the present invention include those of the formulae:

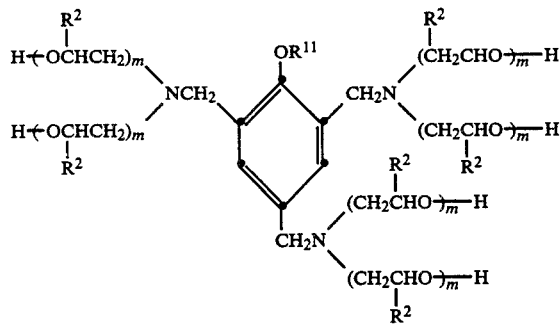

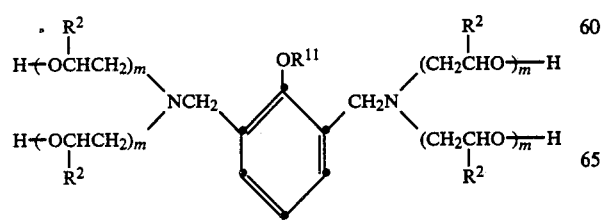

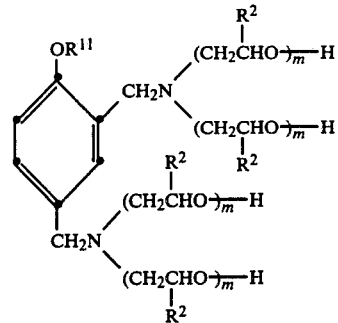

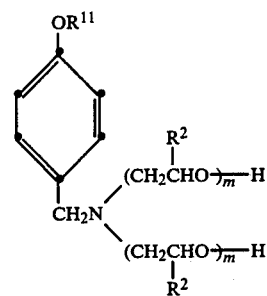

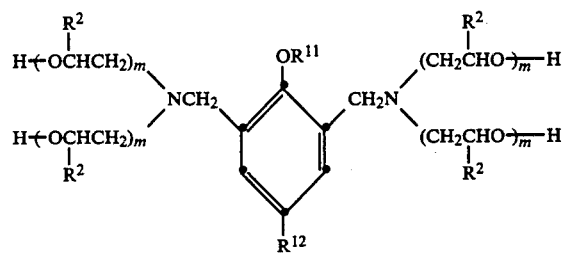

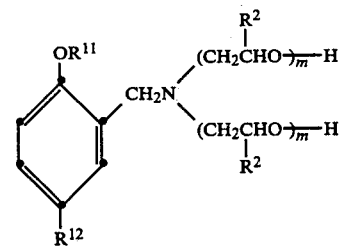

in which $R^2$ is hydrogen or methyl and may be the same or different in each molecule $R^{11}$ is hydrogen,

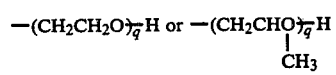

where q is 1 to 4; $R^{12}$ is an alkyl group having 1 to 12 carbon atoms, e.g. a nonyl group and each m is the same or different and is from 1 to 4.

Non-limiting examples of amines of formula IV which may be used are:

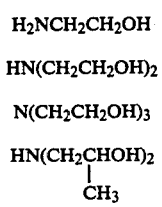

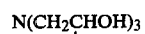

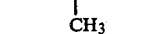

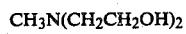

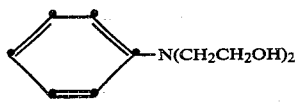

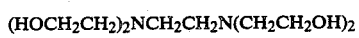

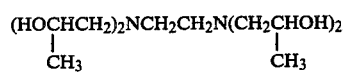

Ethylene diamine/alkylene oxide condensation products such as those sold under the Trade Name Propylan A260® (Diamond Shamrock),

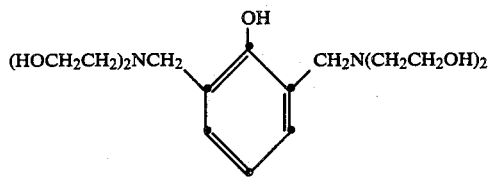

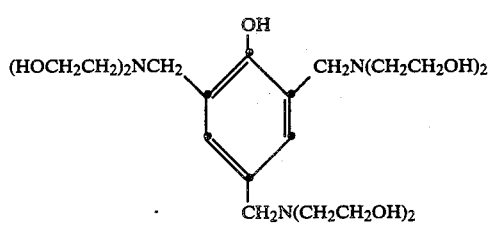

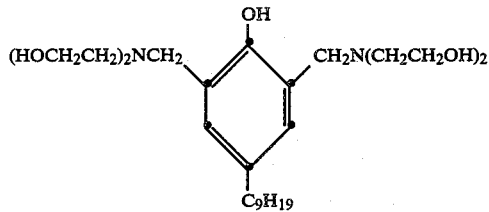

Phenol/formaldehyde/diethanolamine Mannich bases treated with alkylene oxides such as those sold under the Trade Name Thanol R650x® or Thanol R350x® (Texaco), as described in U.S. Pat. No. 3,297,597,

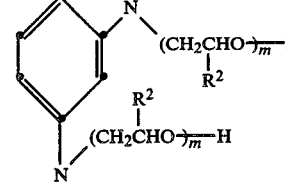

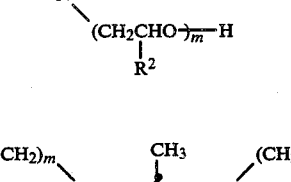

in which $R^2$ is as defined above,

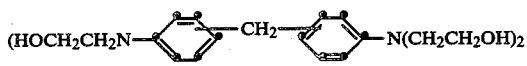

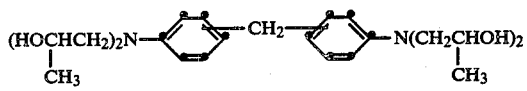

and mixtures of these containing oligomeric compounds of the formula

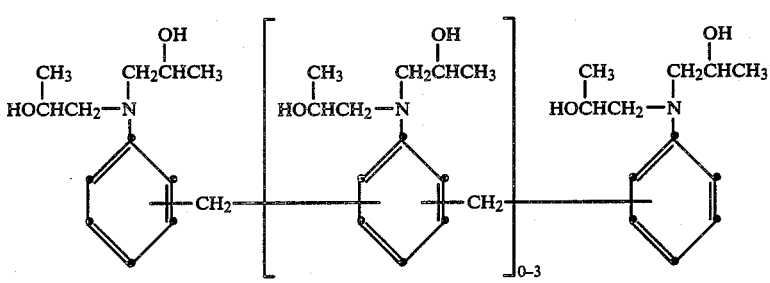

Suitable amines of formula V, which may be used to make the salts of the present invention include:

| | |
|---|---|
| methylamine | diallylamine |
| dimethylamine | propargylamine |
| trimethylamine | cyclobutylamine |
| triethylamine | cyclopentylamine |
| propylamine | cyclohexylamine |
| n-butylamine | cyclooctylamine |
| sec-butylamine | aniline |
| tri-n-butylamine | o-anisidine |
| dodecylamine | p-anisidine |
| allylamine | o-phenylenediamine |
| p-phenylenediamine | 2-aminopyridine |
| N—methylaniline | 2-methoxypyridine |
| o-nitroaniline | 3-chloropyridine |
| o-chloroaniline | ethyleneimine |
| α-naphthylamine | Quinuclidine |
| N,N—dimethylaniline | 1,4-Diazabicyclo[2.2.2]octane |
| benzylamine | ethylenediamine |
| phenethylamine | diethylenetriamine |
| 1-Naphthylmethylamine | triethylenetetramine |
| pyridine | hexamethylene diamine |
| morpholine | dodecamethylene diamine |
| piperidine | 2,4,6-tris(dimethylaminomethyl)phenol. |
| piperazine | |

The amine salts of the invention may be used alone or together with other flame retardants such as those given below for imparting flame retardancy to rigid or flexible polyurethanes or polyisocyanurates. Polyurethanes and polyisocyanurates are prepared by reacting a polyol with a polyisocyanate, in the presence of a blowing agent, if a foam is desired, and a catalyst. The amount of polyisocyanurate is varied to produce the desired product. The present invention is applicable to the whole range of polymers having an isocyanate index of from 1 to 6, preferably from 1 to 4.5.

A further embodiment of the invention concerns a polyurethane or polyisocyanurate having incorporated therein a flame retardant amine salt of the formula Ia and/or Ib

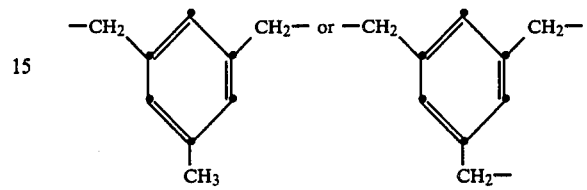

wherein x and y are integers such that the number of negative and positive charges are the same, wherein $R^2$ is hydrogen or methyl, $R^3$ is a $C_2$-$C_4$ alkyl group substituted by 1-3 hydroxyl groups, which may be substituted by an oxyalkylene chain, these being not more than one hydroxyl group on any one carbon atom, $R^4$ and $R^5$ may be the same or different and may be a group as defined for $R^3$, or hydrogen, a $C_1$-$C_4$ alkyl group, a phenyl group, a benzyl group, or a phenyl or benzyl group substituted on the aromatic ring by an alkyl group of 1-12 carbon atoms, a hydroxyl group, which may be substituted by an oxyalkylene chain, and/or 1-3 halogen atoms, or $R^5$ is a group of the formula II

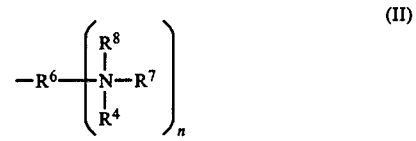

wherein $R^6$ is an alkylene group of 2-4 carbon atoms, a phenylene group, a xylylene group, a diphenyl methane group or is a group of the formula $$-CH_2-\underset{CH_3}{\underset{|}{\bigcirc}}-CH_2- \text{ or } -CH_2-\underset{CH_2-}{\underset{|}{\bigcirc}}-CH_2-$$

in which aromatic rings in a group of $R^6$ may be substituted by an alkyl group of 1-12 carbon atoms, a hydroxyl group, which may be substituted by an oxyalkylene chain, and/or 1-3 halogen atoms, and $R^7$ is hydrogen or methyl, in which cases the nitrogen atom carries a positive charge, or $R^7$ is absent; $R^8$ is hydrogen or a group as defined for $R^3$ and n is 1 or 2;

or $R^4$ and $R^5$ may be joined to form, with the nitrogen, 5 or 6 membered heterocyclic ring, optionally containing an oxygen atom; and $Z^1$, $Z^2$ and $Z^3$ are the same or different and represent hydrogen, a $C_1$-$C_{12}$ straight or branched chain alkyl group, a $C_3$-$C_{12}$ straight or branched chain alkenyl group, a $C_3$-$C_{12}$ straight or branched chain alkynyl group, a $C_4$-$C_{12}$ cycloalkyl group, a phenyl or naphthyl group which may be substituted by a $C_1$-$C_4$ straight or branched chain alkyl group, a $C_1$-$C_4$ alkoxy group, amino, methylamino, halogen or nitro, or a $C_7$-$C_{12}$ aralkyl group;

or $Z^2$ and $Z^3$ together with the nitrogen atom to which they are attached form a saturated or unsaturated 3-7 membered ring system which may optionally contain another hetero atom, and the ring system is optionally substituted by a $C_1$-$C_4$ straight or branched chain alkyl group, a $C_1$-$C_4$ alkoxy group, amino, methylamino, a $C_1$-$C_4$ aminoalkyl group, halogen or nitro;

or $Z^1$ and $Z^2$ and $Z^3$ together with the nitrogen atom to which they are attached from an 8-12 membered bicyclic ring optionally containing another hetero atom; or $Z^1$ is a group of the formula

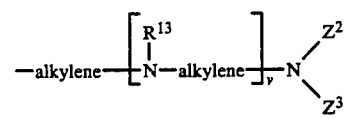

wherein alkylene is a group containing 2 to 12 carbon atoms, v is 0 or an integer from 1 to 5, $R^{13}$ is hydrogen or $C_1$-$C_{16}$ straight or branched chain alkyl group, and $Z^2$ and $Z^3$ are as defined above;

or $Z^1$ is a group of the formula

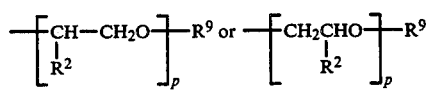

in which $R^2$ is as defined above, $R^9$ is a $C_1$-$C_{12}$ alkyl group and p is an integer from 1-10, preferably from 1-4;

or $Z^3$ is a group of the formula IIa

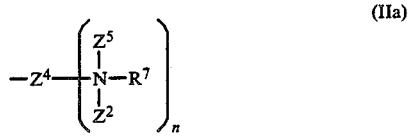

wherein $Z^4$ is an alkylene group of 2-12 carbon atoms, a phenylene group, a xylylene group, a diphenyl methane group or is a group of the formula

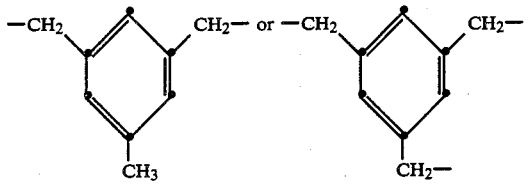

in which aromatic rings in a group $Z^4$ may be substituted by an alkyl group of 1-12 carbon atoms, hydroxyl and/or 1-3 halogen atoms, and $R^7$ is hydrogen or methyl, in which cases the nitrogen atom carries a positive charge, or $R^7$ is absent; $Z^5$ is hydrogen or a group as defined for $Z^1$ and n is 1 or 2; or $Z^2$ and $Z^5$ may be joined to form, with the nitrogen, a 3 to 7 membered heterocyclic ring, optionally containing another hetero atom.

When an amine salt is used which is derived from a polyol, it may be used alone as the sole polyol component for reacting with a polyisocyanate to produce a polyurethane or polyisocyanurate. In most cases where such a high level of flame retardant is not required, the salts may be incorporated into the polyurethane or polyisocyanurate by adding to the reaction mixture used to prepare the polyurethane or polyisocyanurate.

Alternatively the amino salts of the invention may be added to the reactant containing hydroxyl groups (polyester or polyether polyol) prior to its reaction with the polyisocyanate. When amine salts are used which contain hydroxyl groups they will normally react with the isocyanate, as well as the polyol. The viscosity of the polyolamine salt mixture does not change appreciably on storage at room temperature and constant foaming conditions are achieved which do not vary with storage time.

Alternatively a prepolymer may be prepared by reacting amine salts of formula Ia and Ib with a polyisocyanate to give a product with either isocyanate or hydroxyl terminal groups and thereafter the polymer is prepared by further reaction with the polyol or polyisocyanate.

The amount of flame retardant amine salt of the invention which may be incorporated in the polyurethane or polyisocyanurate depends on the level of flame retardancy required. Typically the amount of flame retardant salt in those cases where a polyol is also used, may be from 1 to 200 parts, preferably 3 to 100 parts by weight per hundred parts by weight of polyol.

The amine salts may be mixed with other flame retardant compounds. These may be, for example, halogen-containing compounds such as aliphatic and aromatic bromine compounds, oxyalkylated phosphate esters, chloroalkyl phosphates, phosphonates or tri-aryl phosphates. Examples of suitable compounds are penta-bromo-diphenyl ether, dibromocresyl glycidyl ether, tetra-bromo bisphenol A, dibromoneopentyl glycol, a diol produced by the reaction of tetrabromophthalic anhydride with ethylene oxide and/or propylene oxide, tris(chloroethyl)phosphate, tris(monochloropropyl)-phosphate, diethyl bis-(hydroxyethyl)-aminomethyl phosphate, and isopropylated or t-butylated phenyl phosphate mixtures as described in British Patent Specification No. 1 146 173, tricresyl phosphate, trixylyl phosphate and cresyl diphenyl phosphate. The ratio of amine salt to other flame retardant compounds may be from 5:95 to 95:5.

The polyurethane and polyisocyanurate compositions may also contain methylphosphonic acid and its monomethyl or dimethyl esters which are not reacted with the amine present although, preferably, acidic additives are not present in the formulation.

The isocyanates and polyols used in making the polyurethane or polyisocyanurate can be any of these known in the art.

The isocyanate is ordinarily a liquid such as toluene di-isocyanate, methylene diphenyl di-isocyanate, polymeric methylene diphenyl di-isocyanate, hydrogenated methylene diphenyl di-isocyanate, hexamethylene di-isocyanate, isophorone di-isocyanate, and any polyisocyanate prepolymer containing two or more unreacted isocyanate radicals and the like. Conventionally, the toluene di-isocyanate used in the invention contains isomers of 2,4- and 2,6-toluene di-isocyanate. The concentration of these isomers is not critical.

The polyol for rigid foam may be a polyfunctional active hydrogen compound derived from the reaction of a polyhydroxylic compound such as glycerol, sucrose, sorbitol, trimethylol propane, pentaerythritol, triethanolamine, or an amine such as ethylenediamine, polyaromatic amine, or an aromatic Mannich base with propylene oxide and/or ethylene oxide.

Generally for production of flexible polyurethane foams the polyols are polyether polyols such as polyoxyethylene/oxypropylene diols, polyoxyethylene/oxypropylene triols, castor oil and methylglucoside polyether polyols having average molecular weights in the range of approximately 250-6500. Other polyols which may be used in place of polyether polyols are the polyester polyols, such as the reaction products of an aliphatic difunctional carboxylic acid e.g. adipic acid, sebacic acid, with a di- or tri-functional hydroxy compound e.g. ethylene glycol, diethylene glycol, propylene glycol, 1,4-butylene glycol and butane triol.

Additionally polyols such as glycerol, hexane triol, butane triol, trimethylol propane, trimethylol ethane, and pentaerythritol, may be included in the polymerisation reaction with the polyol to maintain a desirable stoichiometrically balanced isocyanate to hydroxyl ratio.

In preparing the foamed polyurethanes and polyisocyanurates there can be used any of the conventional basic catalysts such as, for example, sodium hydroxide, sodium acetate, tertiary amines or materials which generate tertiary amines such as trimethylamine, triethylene diamine, N-methyl morpholine, N,N-dimethyl cyclohexylamine, and N,N-dimethyl aminoethanol. Also applicable are metal compounds such as hydrocarbon tin alkyl carboxylates, dibutyl tin diacetate, dibutyl tin dioctoate dibutyl tin dilaurate and stannous octoate; as well as other compounds intended to promote trimerisation of the isocyanate such as, 2,4,6-tris(N,N-dimethylamino-methyl)phenol, 1,3,5-tris(N,N-dimethyl-3-aminopropyl)-S-hexahydrotriazine, potassium octoate, potassium acetate and catalysts such as those sold under the Trade Names DABCO TMR ® and POLYCAT 43 ®.

Many other catalysts may be substituted for those listed above, as desired. The amount of catalyst used may be in the range of about 0.05% to about 5% or more by weight based upon the total weight of poly(s) employed. Mixtures of the above and/or other catalysts may also be utilised.

To impart a foamed or cellular structure to the blended polyolpolyisocyanate mixture, a suitable blowing agent or system of blowing agents must be added or produced in-situ. Suitable blowing agents include the liquid but relatively volatile halogenated hydrocarbons such as dichlorodifluoromethane, trichlorofluoromethane, and methylene chloride. These are added as liquids in quantities of about 5% to about 50%, by weight of the polyol, to the one or more components of the polyol-polyisocyanate mixture and are substantially volatilised in the liquid mixture to effect cell formation. Subsequently, the mixture cures to its final cellular shape.

Although the halogenated hydrocarbons are especially desirable as blowing agents when exceptional insulative properties are derived, other blowing agents, such as carbon dioxide generated by adding water to the polyol or simultaneously with the addition of the polyisocyanate, can be utilised especially for flexible open-celled foams.

It should also be noted that foaming may also be effected by combining the use of a blowing agent with the addition of water to the polyol.

In order to obtain relatively uniform distribution of the various components of the liquid system and to achieve the derived formation of bubbles, an emulsifier and/or surfactant may be incorporated into the mixture. These materials are physical in their effect and are not always necessary, especially if denser foams are desired. Any of the many hundreds of conventional surfactants can be used in amounts of up to 4% based on the weight of polyol used. Suitable surfactants are polydimethylsiloxane and polydimethylsiloxane polyalkylene copolymers, and the like known in the art.

It is also within the scope of the present invention to employ other materials in the compositions where one desires to achieve a particular end result. Such materials include, without limitation, adhesion promoters, antioxidants, antistatic agents, antimicrobials, colourants, heat stabilisers, light stabilisers, pigments, plasticisers, preservatives, ultraviolet stabilisers, and fillers as described in Modern Plastics Encyclopedia. Volume 58, Number 10A, pages 170–187.

The invention is illustrated by the following examples in which "parts" are parts by weight.

EXAMPLE 1

49.6 Parts of dimethylmethylphosphonate and 245.6 parts of a p-nonyl phenol/formaldehyde/diethanolamine Mannich base reacted with propylene oxide (sold under the Trade Name Thanol R650x ®) are heated with stirring to 120° C. under a nitrogen atmosphere. Stirring is continued for 4 hours at 120° C. The reaction mixture is then transferred to a rotary evaporator and volatile materials removed by heating at 90° C. under a pressure of 133 Pa for 2 hours. The residual product comprises 266 parts of a viscous liquid. The $^{31}$P nmr chemical shift of the product is 23.8 ppm downfield, characteristic of an amine/phosphonic acid salt.

EXAMPLE 2

By a method similar to that described in Example 1 81.8 parts of dimethylmethylphosphonate and 202.6 parts of Thanol R650x ® are reacted to give 256 parts of a viscous liquid product, $^{31}$P chemical shift=23.5 df (downfield).

EXAMPLE 3

By a method similar to that described in Example 1 24.8 parts of dimethylmethylphosphonate and 106.0 parts of a phenol/formaldehyde/diethanolamine Mannich base reacted with propylene oxide (sold under the Trade Name Thanol R350x ®) are reacted to give 128.5 parts of a viscous liquid product, $^{31}$P chemical shift=24.2 df.

EXAMPLE 4

By a method similar to that described in Example 1 49.6 parts of dimethylmethylphosphonate and 106.0 parts of Thanol R350x ® are reacted to give 155.2 parts of a viscous liquid product, $^{31}$P chemical shift=24.4 df.

EXAMPLE 5

By a method similar to that described in Example 1 62.0 parts of dimethylmethylphosphonate and 74.5 parts of triethanolamine react exothermically to give 132.2 part of a viscous liquid product, $^{31}$P chemical shift=21.4 df.

Elemental analysis of the product gives C=38.8%, H=9.7%, N=5.2%, P=11.1%. $C_9H_{24}NO_6P$ requires C=39.6%, H=8.8%, N=5.1%, P=11.4%.

The product is essentially the amine/phosphonate salt.

EXAMPLE 6

By a method similar to that described in Example 1 12.4 parts dimethylmethylphosphonate and 10.5 parts of diethanolamine react exothermically to give 22.3 parts of a viscous liquid product $^{31}$P chemical shift—22.0 df.

Elemental analysis of the product gives C=36.0%, H=9.4%, N=6.0%, P=13.3%. $C_7H_{20}NO_5P$ requires C=36.7%, H=8.7%, N=6.1%, P=13.5%.

The product is essentially the amine/phosphonate salt.

EXAMPLE 7

By a method similar to that described in Example 1 31.0 parts of dimethylmethylphosphonate and 67.5 parts of an ethylene diamine/alkylene oxide condensate (sold under the Trade Name Propylan A260 ®) are reacted to give 96.1 parts of a viscous liquid product, $^{31}$P chemical shift=21.3 df.

EXAMPLE 8

11.0 Parts of methylphosphonic acid monomethyl ester and 61.4 parts of Thanol R650x ® are heated with stirring to 80° C. Stirring is continued for half and hour at 80° C. The reaction mixture is then transferred to a rotary evaporator and any volatile materials removed by heating at 80° C. under a pressure of 133 Pa for 1 hour. The residual product comprises 68 parts of a viscous liquid, $^{31}$P chemical shift=24.9 df.

EXAMPLE 9

By a method similar to that described in Example 8 22.0 parts of methylphosphonic acid monomethyl ester and 61.4 parts of Thanol R650x ® are reacted to give 80.2 parts of a viscous liquid product, $^{31}$P chemical shift=25.2 df.

EXAMPLE 10

By a method similar to that described in Example 8 22.0 parts of methylphosphonic acid monomethyl ester and 29.8 parts triethanolamine are reacted to give 51.0 parts of a viscous liquid product. $^{31}$P chemical shift=19.6 df.

EXAMPLE 11

19.2 Parts of methylphosphonic acid and 122.8 parts of Thannol R650x ® are heated with stirring to 100° C. Stirring is continued at 100° C. for half an hour. The reaction mixture is transferred to a rotary evaporator and any volatile materials removed by heating at 80° C. under a pressure of 133 Pa for 1 hour. The residual product comprises 141.6 parts of a very viscous liquid, $^{31}$P chemical shift=22.0 df.

EXAMPLE 12

By a method similar to that described in Example 11 19.2 parts of methylphosphonic acid and 59.6 parts of triethanolamine are reacted to give 76.7 parts of a viscous liquid product $^{31}$P chemical shift=20.5 df.

EXAMPLE 13

25 g (0.22 mole) 1,4-diazabicyclo[2.2.2]octane and 70 g (0.56 mole) dimethylmethylphosphonate are mixed and heated at 120° C. for 3 hours under an atmosphere of nitrogen. After cooling to room temperature the apparatus is adapted for vacuum distillation and the excess dimethylmethylphosphonate removed at 1596 Pa pressure by heating to 95° C. 77.2 g (97.4%) of straw coloured liquid are obtained which shows the major peak at 20.9 downfield with respect to H$_3$PO$_4$ on $^{31}$P nmr spectroscopy.

EXAMPLE 14

47 g (0.5 mole) 2-aminopyridine are heated to 140° C. and 124 g (1 mole) dimethylmethylphosphone added dropwise over 5 hours. The reaction mixture is raised to 180° C. and maintained at this temperature for 9 hours. The reaction mixture is cooled to 50° C. and the apparatus adapted for distillation. Unreacted starting materials are removed at a pressure of 1596 Pa up to a flask temperature of 120° C. The reaction mixture is cooled to 30° C. and the dark brown liquid dissolved in 250 ml chloroform. On cooling to 5° C. there is deposited from solution 30 g of a white crystalline compound which has the following analysis: C 44.1%, H 6.09%, N 12.84% and P 13.95%. Calculated for C$_8$H$_{15}$N$_2$O$_3$P: C 44.0%, H 6.88%, N 12.84% and P 14.22%.

The compound melts at 220° C. with decomposition. $^1$H nmr and $^{31}$P nmr indicate that the compound is

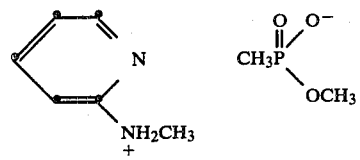

EXAMPLE 15

The chloroform filtrate from Example 14 is evaporated at 60° C. for 3 hours. A dark brown liquid is obtained having the following analysis: C 38.01%, H 7.21%, N 8.34% and P 17.97%. Calculated for C$_{11}$H$_{24}$N$_2$O$_6$P$_2$: C 38.60%, H 7.02%, N 8.18% and P 18.13%.

$^1$H nmr and $^{31}$P nmr indicate that the compound is

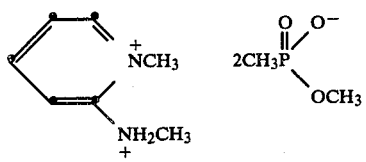

EXAMPLE 16

50.5 g (0.5 mole) triethylamine and 62 g (0.5 mole) dimethylmethylphosphonate are dissolved in 250 mls mesitylene and the mixture heated to reflux for a total of 22.5 hours. During this time the reflux temperature increases from 133° C. to 154° C. The reaction product separates from solution as a brown coloured liquid. The reaction mixture is cooled to 30° C. and the apparatus adapted for distillation. Mesitylene and unreacted starting materials are removed under vacuum firstly at a pressure of 1596 Pa then at 133 Pa up to a temperature of 190° C. The resulting dark coloured liquid is dissolved in methanol and the resulting solution decolourised by treatment with carbon. After evaporation to remove the methanol there is obtained 87 g (77.3%) of a straw coloured liquid having the following analysis: C 47.69%, H 11.05%, N 6.49% and P 13.96%. Calculated for C$_9$H$_{24}$NO$_3$P: C 48.0%, H 10.67%, N 6.22%, P 13.77%.

The reaction product shows a single peak at 21.1 downfield with respect to H$_3$PO$_4$ on $^{31}$P nmr spectroscopy.

EXAMPLE 17

124 g (1 mole) dimethylmethylphosphonate are heated to 140° C. under an atmosphere of nitrogen, 30 g (0.5 mole) 1,2-diaminoethane are added dropwise over 6 hours as to maintain the temperature at 140° C. A dark brown resinous material is obtained after cooling to room temperature. This material is decolourised by dissolving in methanol (300 mls) and treating with carbon. On concentrating to a volume of 200 mls and cooling in an ice-bath a pale coloured crystalline material is deposited which is isolated by filtration and dried under vacuum. 67 g of an off-white solid melting at 108°–112° C. are obtained. Analysis of this material shows C 30.03%, H 8.66%, N 9.39% and P 20.0%. Calculated for C$_8$H$_{26}$N$_2$O$_6$P$_2$: C 31.16%, H 8.44%, N 9.09% and P 20.13%.

The compound shows a single peak at 28.6 downfield with respect to H$_3$PO$_4$ on $^{31}$P nmr spectroscopy.

EXAMPLE 18

124 g (1 mole) dimethylmethylphosphonate was heated at 140° C. under a nitrogen atmosphere whilst 34.3 g (0.33 moles) diethylene triamine are added over 5 hours. The reaction mixture is cooled to 30° C. and the apparatus adapted for vacuum distillation. Unreacted materials are removed at a 1596 Pa pressure up to a flask temperature of 150° C. 155 g (97.9% theory) of a dark brown resinous material are obtained. Elemental analysis shows: C 31.15%, H 8.65%, N 8.29% and P 19.56%. Calculated for $C_{13}H_{40}N_3O_9P_3$: C 32.84, H 8.42%, N 8.84% and P 19.58%.

$^{31}P$ nmr spectroscopy shows two peaks the major one at 22.6 and the minor one at 21.4 both downfield respectively to $H_3PO_4$.

EXAMPLE 19

62 g (0.5 mole) dimethylmethylphosphonate was heated at 140° C. whilst 39.5 g (0.5 mole) pyridine is added dropwise over 4 hours. The mixture is heated a further 2 hors at 140° C. then cooled to 30° C. The apparatus is adapted for distillation and unreacted starting materials are removed at a pressure of 39.9 Pa and a maximum temperature of 100° C. Traces of pyridine are removed by dissolving the dark reaction mass in 200 mls water and treating the resulting solution with carbon. After evaporation of the solution to constant weight 86.2 g (84.9% theory) of a dark brown resin are obtained. Analysis shows: C 47.98%, N 7.09%, N 6.09% and P 16.07%. Calculated for: C 47.29%, H 6.89%, N 6.89% and P 15.27%.

$^{31}P$ nmr spectroscopy shows a single peak at 33,4 downfield with respect to $H_3PO_4$.

EXAMPLE 20

34 g (0.5 mol) imidazole are heated at 140° C. and 124 g (1 mole) dimethylmethylphosponate added over 4 hours. The reaction temperature is slowly raised to 185° C. over 5 hours and heated at this temperature for a further 6 hours. The reaction mixture is cooled to 30° C. and the apparatus adapted for vacuum distillation. Unreacted starting materials are removed by distillation at 39.9 Pa up to a flask temperature of 110° C. 122.5 g (77.5% theory) of a dark brown resin are obtained having the following analysis: C 34.81%, H 7.43%, N 9.11% and P 19.49%. Calculated for $C_9H_{22}N_2O_6P_2$: C 34.17%, H 6.96%, N 8.86% and P 19.62%.

EXAMPLE 21

43 g (0.5 mole) piperazine are heated at 140° C. and 124 g (1 mole) dimethylmethylphosphonate are added dropwise over 5 hours then the reaction mass is heated at 150° C. for 4.5 hours. After cooling to 30° C. the amber coloured resin is dissolved in 125 mls ethanol. The resulting solution is cooled to −70° C. and 53.1 g of a white crystalline compound isolated by filtration. This compound has a melting point of 251°–253° C. with decomposition and has the following elemental analysis: C 34.96%, H 8.77%, N 8.51% and P 19.17%. Calculated for $C_{10}H_{28}N_2O_6P_2$: C 35.92%, H 8.38%, N 8.38% and P 18.56%.

$^{31}P$ nmr spectroscopy shows a single peak at 24.6 downfield with respect to $H_3PO_4$.

EXAMPLE 22

62 g (0.5 mole) dimethylmethylphosphonate are heated at 140° C. and 42.5 g (0.5 mole) piperidine added over 5 hours. Heating at 140° C. is continued for a further 7 hours. After cooling to 30° C. the apparatus is adapted for distillation and unreacted starting materials removed at 53.2 Pa pressure up to a flask temperature of 150° C. 84.5 g (80.9% theory) of a brown viscous liquid are obtained having the following elemental analysis: C 45.38%, H 9.50%, N 7.05% and P 15.16%. Calculated for $C_8H_{20}NO_3P$: C 45.93%, H 9.57%, N 6.70% and P 14.83%.

EXAMPLE 23

62 g (0.5 mole) dimethylmethylphosphonate is heated at 140° C. 43.5 g (0.5 mole) morpholine is added dropwise over 4 hours. The reaction mixture starts to reflux and the temperature drops to 134° C. The reaction mixture is heated at this temperature for a further 3 hours. After removing unreacted starting materials by vacuum distillation at 39.9 Pa pressure up to a flask temperature of 120° C. 70 g of a dark viscous liquid are obtained.

Elemental analysis shows: C 39.47%, H 8.43%, N 6.22% and P 14.8%. Calculated for $C_7H_{18}NO_4P$: C 39.81%, H8.53%, N 6.63% and P 14.70%.

EXAMPLE 24

30 g (0.5 mole) 1,2-diaminoethane are added to a solution of 48 g (0.5 mole) methylphosphonic acid in 200 ml methanol over 1 hour. The temperature being maintained at 25° C. by cooling in an ice/water bath. After stirring for a further 1 hour the reaction mixture is diluted with 50 ml methanol and the reaction product isolated by filtration. After drying under vacuum at 50° C. there are obtained 75.1 g (96.3% of theory) of a white crystalline material melting at 242°–244° C. and having the following analysis: C 22.79%, H 8.2%, N 17.46% and P 19.93%. Calculated for $C_3H_{13}N_2O_3P$: C 23.08% H 8.39% N 17.9% and P 19.84%.

EXAMPLE 25

107 g (1 mole) benzylamine are added over 1 hour to 124 g (1 mole) dimethylmethylphosphonate at 140° C. under a nitrogen atmosphere. The reaction mixture is heated at 140° C. for a further 3 hours then cooled at 60° C. The apparatus is adapted for vacuum distillation and unreacted starting material removed at 1596 Pa pressure up to a flask temperature of 140° C. There are obtained 220.5 g of yellow coloured liquid, which is extremely hygroscopic, having a phosphorus content of 13.05%. Calculated for $C_{10}H_{18}NO_3P$: P=13.39%.

EXAMPLE 26

44 g (0.5 mole) N,N'-dimethylethylenediamine are added over 1 hour to 124 g (1 mole) dimethylmethylphosphonate at 140° C. under an atmosphere of nitrogen. During this addition an exothermic reaction causes the temperature to rise to 165° C. The reaction mixture is cooled to 140° C. and maintained at this temperature for a further 3 hours, after which time it is cooled to 50° C. and the apparatus adapted for vacuum distillation. Unreacted starting materials are removed by distillation up to a temperature of 140° C. at 1596 Pa pressure. There are obtained 153.8 g (91.5%) of a brown coloured hydroscopic liquid having the following analysis: C 35.17%, H 8.58%, N 8.65%, P 18.44%. Calculated for $C_{10}H_{30}N_2O_6P_2$: C 35.71%, H 8.93,% N 8.33% and P 18.45%.

EXAMPLE 27

75 g (1 mole) 2-methoxyethylamine are added over 1 hour to 124 g (1 mole) dimethylmethylphosphonate at 140° C. under an atmosphere of nitrogen. The reaction is maintained at 140° C. for a further 3 hours then cooled to 40° C. The apparatus is adapted for vacuum distillation and unreacted starting materials are removed by slowly heating up to a maximum temperature of 140° C. at a pressure of 1596 Pa. There are provided 158.8 g (79.8% of theory) of an amber coloured liquid having the following analysis: C 35.95%, H 9.15%, N 7.31% and P 15.89%. Calculated for $C_6H_{18}NO_4P$: C 36.17%, H 9.12%, N 7.03% and P 15.54%.

EXAMPLE 28

64.2 (0.6 moles) N-methylaniline are added dropwise over 1 hour to a solution of 66 g (0.6 mole) monomethylmethylphosphonate in 100 ml methanol cooled at <15° C. by an ice/water bath. The resulting solution is stirred for a further 1 hour then the methanol is removed by vacuum distillation. 130.1 g of a dark brown liquid are obtained having analysis C 49.74%, H 7.46%, N 6.34% and P 14.60%. Calculated for $C_9H_{16}NO_3P$: C 49.77%, H 7.37%, N 6.45% and P 14.29%. The product shows a single peak at 27.2 downfield with respect to $H_3PO_4$ on $^{31}P$ nmr spectroscopy.

EXAMPLE 29

72.6 g (0.6 mole) N,N-dimethylaniline are added over 1 hour to a solution of 66 g (0.6 mole) monomethylmethylphosphonate in 100 ml methanol whilst cooling at <15° C. by means of an ice/water bath. The resulting solution is stirred for a further 1 hour then the methanol is removed by vacuum distillation. 138.1 g of a pale brown liquid are obtained having the following analysis C 51.67%, H 8.00%, N 5.80% and P 13.65%. Calculated for $C_{10}H_{18}NO_3P$: C 51.94%, H 7.79%, N 6.06% and P 13.42%.

The product shows a single peak at 28.0 downfield with respect of $H_3PO_4$ on $^{31}P$ nmr spectroscopy.

EXAMPLE 30

55.5 g (0.5 mole) quinuclidine are heated to 120° C. under an atmosphere of nitrogen and 62 g (0.5 mole) dimethylmethylphosphonate are added dropwise over 1 hour. The reaction mixture is maintained at 120° C. for a further 4 hours. The reaction product is cooled to 40° C. and dissolved in 200 ml methanol and treated with activated carbon. After filtration and drying under vacuum there are obtained 115.1 g (97.9% theory) of a pale yellow hygroscopic liquid. The product had the following analysis: C 46.29%, H 9.52% N 5.26% and P 11.56%. Calculated for $C_{10}H_{22}NO_3P.1.5H_2O$: C 48.80%, H 9.54%, N 5.34% and P 11.83%.

EXAMPLE 31

44 g (0.5 mole) N,N-dimethylethylenediamine are heated to 140° C. under an atmosphere of nitrogen. 124 g (1 mole) dimethylmethylphosphonate are added dropwise over 1 hour. The reaction mixture is maintained at 140° C. for a further 3 hours. After cooling to 40° C. the reaction apparatus is adapted for distillation and unreated starting materials are removed at 1596 Pa pressure up to a temperature of 140° C. There are obtained 149.6 g (89.0% of theory) of brown liquid which partially crystallised on standing. The product had the following analysis: C 35.39%, H 8.61%, N 8.43% and P 18.41%. Calculated for $C_{10}H_{30}N_2O_6P_2$: C 35.71%, H 8.93%; N 8.33% and P 18.45%.

EXAMPLE 32

148.5 g (1.5 mole) cyclohexylamine are added over 2 hours to 186 g (1.5 mole) dimethylmethylphosphonate at 140° C. under an atmosphere of nitrogen. The reaction mixture is maintained at 140° C. for a further 2 hours then cooled to 70° C. The apparatus is adapted for distillation and unreacted starting materials are removed by distillation at 1596 Pa pressure up to a temperature of 140° C. 317.1 g (94.8% of theory) of a pale yellow viscous resinous material are obtained having analysis: C 48.46%, H 9.95%, N 5.98% and P 13.67%. Calculated for $C_9H_{22}NO_3P$ C 48.43%: H 9.87%, N 6.28% and P 13.90%. $^{31}P$ nmr spectroscopy shows a single peak at 22.9 downfield with respect to $H_3PO_4$.

EXAMPLE 33

46.5 g (0.5 mole) aniline are added over 30 mins. to a solution of 48 g (0.5 mole) methylphosphonic acid in 200 ml methanol at <15° C. The white crystalline compound deposited from solution is isolated by filtration and dried under vacuum. There are obtained 76.7 g of material melting at 144°–146° C., and having the following analysis: C 44.33%, H 6.37%, N 7.36% and P 16.60%. Calculated for $C_7H_{12}NO_3P$: C 44.44%, H 6.35%, N 7.41% and P 16.40%.

EXAMPLES 34–69

The following examples illustrate the ease with which flame retardant rigid foamed polyurethane compositions may be produced from polyols and polymeric diphenyl methane diisocyanate in accordance with the present invention.

The following foam formulation is utilised to show the effect of flame retardant.

| Reactant | Concentration (parts) |
| --- | --- |
| Thanol R650x ®[1] | as indicated |
| Water | 0.2 |
| Silicone surfactant | 2 |
| trichloro fluoro methane | 40 (to foam density 30 ± 1 kg/m$^3$) |
| Flame retardant | as indicated |
| Suprasec DND ®[2] | to index of 1.05 |

[1]An aromatic polyol
[2]A polymeric diphenyl methane diisocyanate

The above ingredients are mixed together for 10 seconds in a high speed stirrer (2000 rpm) at room temperature, with the isocyanate being added last, and then poured immediately into a cardboard mould. The exothermic reaction which ensues is allowed to free rise the foam. The length of time from the addition of the isocyanate to the formation of a creamy consistency of the mixture is given as the cream time. The time required for the foam to attain the maximum height is given as the rise time. The time until the foam is not longer tacky is designated as the non-tack time. After attainment of the non-tack time, the foam is aged for 3 days at ambient temperature.

Test specimens are cut from the foam after 3 days storage and subjected to the Limiting Oxygen Index Test and DIN 4102 B2 vertical Burn test. Results are shown in the Table below, and as a comparison the same foam material is produced without flame retardant. The foams obtained from Examples 34–69 exhibited no splits, no distortion, and no scorching.

|     | Product of Example | | Foam Parameters | | | | Oxygen Index % | DIN 4102 B2 Test | | |
| --- | --- | --- | --- | --- | --- | --- | --- | --- | --- | --- |
| Ex. | Number | Level (parts) | Polyol parts | Cream Time (sec) | Rise Time (sec) | Non-tack Time (sec) | | Time to specification mark (sec) | Maximum flame height (cm) | Burn Time (sec) |
| 34 | None | None | 100 | 17 | 70 | 120 | <21 | 3 | >20 | >60 Burns comp. |
| 35 | 1 | 65 | 45 | 12 | 18 | 25 | 23.8 | — | 12 | 17 |
| 36 | 2 | 38 | 72 | 10 | 18 | 24 | 24.7 | — | 14 | 17 |
| 37 | 3 | 52.7 | 57.3 | 14 | 22 | 34 | 24.3 | — | 14 | 12 |
| 38 | 4 | 31.3 | 78.7 | 15 | 30 | 40 | 24.3 | — | 13 | 10 |
| 39 | 5 | 19.7 | 90 | 19 | 25 | 35 | 24.5 | — | 13 | 13 |
| 40 | 6 | 18.3 | 91.7 | 10 | 23 | 39 | 22.4 | — | 14 | 10 |
| 41 | 7 | 31 | 80 | 16 | 20 | 34 | 23.9 | 7 | 15 | 14 |
| 42 | 8 | 52.4 | 57.6 | 21 | 52 | 81 | 23.8 | — | 12 | 8 |
| 43 | 9 | 34.1 | 74.8 | 12 | 20 | 30 | 24.2 | 5 | 15 | 15 |
| 44 | 10 | 25.7 | 100 | 10 | 22 | 34 | 24.6 | — | 14 | 15 |
| 45 | 11 | 58 | 49.7 | 10 | 15 | 23 | 24.1 | — | 14 | 14 |
| 46 | 12 | 41.4 | 100 | 11 | 29 | 51 | 24.6 | 10 | 15 | 14 |
| 47 | 13 | 10 | 100 | 9 | 21 | 35 | 22.7 | 0 | 13 | 10 |
| 48 | 13 | 16 | 100 | 8 | 20 | 37 | 23.5 | 0 | 13 | 9 |
| 49 | 14 | 10 | 100 | 21 | 75 | 140 | 23.6 | 0 | 13 | 10 |
| 50 | 15 | 10 | 100 | 10 | 20 | 34 | 25.0 | 0 | 12 | 12 |
| 51 | 16 | 10 | 100 | 10 | 14 | 19 | 24.2 | 5 | 16 | 13 |
| 52 | 17 | 13 | 100 | 12 | 24 | 30 | 24.3 | 0 | 12 | 9 |
| 53 | 18 | 13 | 100 | 7 | 15 | 29 | 24.4 | 0 | 14 | 11 |
| 54 | 19 | 10 | 100 | 11 | 16 | 26 | 24.6 | 0 | 13 | 10 |
| 55 | 20 | 10 | 100 | 8 | 15 | 27 | 24.8 | 0 | 12 | 15 |
| 56 | 21 | 10 | 100 | 21 | 79 | 134 | 25.0 | 0 | 12 | 7 |
| 57 | 22 | 10 | 100 | 9 | 16 | 28 | 25.0 | 0 | 14 | 15 |
| 58 | 23 | 10 | 100 | 9 | 19 | 31 | 25.1 | 0 | 12 | 11 |
| 59 | 24 | 10 | 100 | 22 | 75 | 138 | 22.9 | 0 | 14 | 10 |
| 60 | 25 | 10 | 100 | 4 | 10 | 20 | 24.7 | 0 | 11 | 14 |
| 61 | 26 | 10 | 100 | 10 | 19 | 34 | 25.4 | 0 | 12 | 12 |
| 62 | 27 | 10 | 100 | 9 | 19 | 32 | 25.7 | 0 | 13 | 11 |
| 63 | 28 | 10 | 100 | 9 | 26 | 56 | 24.3 | 6 | 15 | 12 |
| 64 | 29 | 10 | 100 | 15 | 34 | 77 | 24.1 | 6 | 17 | 14 |
| 65 | 30 | 10 | 100 | 4 | 11 | 28 | 24.8 | 7 | 15 | 10 |
| 66 | 31 | 10 | 100 | 5 | 16 | 28 | 25.2 | 8 | 15 | 12 |
| 67 | 32 | 10 | 100 | 5 | 17 | 30 | 23.7 | 4 | 17 | 12 |
| 68 | 33 | 10 | 100 | 8 | 34 | 70 | 24.9 | 8 | 15 | 12 |
| 69 | 17 | 19.5 | 86 | 13 | 27 | 37 | 25.2 | 0 | 12 | 8 |

EXAMPLES 70 TO 73

The following examples illustrate the ease with which flame retardant flexible foamed polyurethane compositions may be produced from polyols and toluene diisocyanate in accordance with the present invention.

The following foam formulation was utilised to show the effect of flame retardant.

| Reactant | Concentration (parts) |
| --- | --- |
| Propylan B383 ® | 100 |
| Silicone surfactant | 1 |
| Water | 4 (to foam density 28 + 1 kg/m³) |
| Stannous octoate | 0.3 |
| Propamine A ® | 0.4 |
| Flame retardant | as indicated |
| Toluene diisocyanate | to index of 1.08 |

The above ingredients are mixed together in a high speed hand held stirrer (2000 rpm) at room temperature for 10 second and then poured as quickly as possible into a cardboard mould. The exothermic reaction which ensues is allowed to free-rise the foam. After allowing the foam to cure at ambient temperature for 7 days it is found to have the physical properties shown in the table below.

For comparison a foam is prepared from the same reactants without flame retardant whilst maintaining the isocyanate index at 1.08 in the same manner. Test specimens are cut from the foam after 3 days storage and subjected to the BS4735 horizontal burn test. The results are shown in the table below.

| | Product of Example | | BS4735 Burn Test | |
| --- | --- | --- | --- | --- |
| Example | Number | Level (parts) | Burn length (mms) | Burn time (sec) |
| 70 | | None | Burns completely | |
| 71 | | 22.6 | 61 | 52 |
| 72 | 13 | 13.7 | 90 | 65 |
| 73 | 17 | 10 | 28 | 33 |
| | | 13.7 | 90 | 65 |

EXAMPLES 75 TO 75

The storage stability of a polyol formulation containing products of the present invention is illustrated by the following. Two formulations are prepared and their viscosity measured after production and after 39 days. In one case there is only a very small difference and in the other case there has been no change in viscosity.

| | Example 74 | Example 75 |
| --- | --- | --- |
| Formulation | | |
| Product of Example 1 | 65 parts | 0 |
| Product of Example 2 | 0 | 38 |
| Thanol R650X ® | 45 | 72 |
| Silicone DC 193 ® | 2 | 2 |
| Refrigerant 11 | 40 | 40 |

-continued

|  | Example 74 | Example 75 |
|---|---|---|
| Isopropylated phenyl phosphate | 15 | 15 |
| Properties |  |  |
| Viscosity mm²/S at day 0 | 1463 | 780 |
| Viscosity mm²/S at day 39 | 1446 | 780 |

We claim:

1. A rigid polyurethane or polyisocyanurate prepared from a reaction mixture comprising active hydrogen compounds and polyisocyanates and a flame retardant amount of an amine salt of the formula Ia and/or Ib

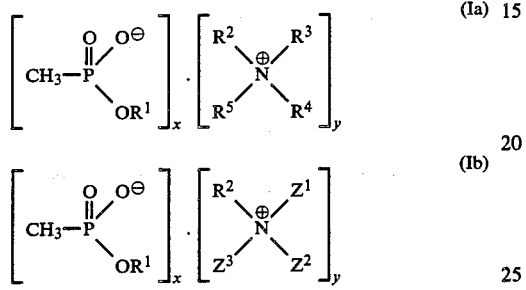

wherein x and y are integers such that the number of negative and positive charges are the same, $R^1$ is hydrogen, methyl or a negative charge, $R^2$ is hydrogen or methyl, $R^3$ is a $C_2$-$C_4$ alkyl group substituted by 1-3 hydroxyl groups, which may be substituted by an oxyalkylene chain, these being not more than one hydroxyl group on any one carbon atom, $R^4$ and $R^5$ may be the same or different and may be a group as defined for $R^3$, or hydrogen, a $C_1$-$C_4$ alkyl group, a phenyl group, a benzyl group, or a phenyl or benzyl group substituted on the aromatic ring by an alkyl group of 1-12 carbon atoms, a hydroxyl group, which may be substituted by an oxyalkylene chain, and/or 1-3 halogen atoms, or $R^5$ is a group of the formula II

wherein $R^6$ is an alkylene group of 2-4 carbon atoms, a phenylene group, a xylylene group, a diphenyl methane group or is a group of the formula

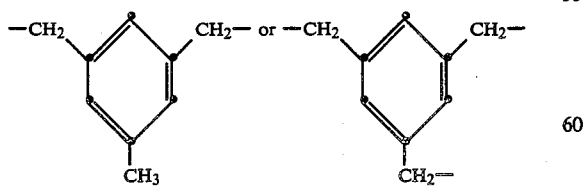

in which aromatic rings in a group $R^6$ may be substituted by an alkyl group of 1-12 carbon atoms, a hydroxyl group, which may be substituted by an oxyalkylene chain, and/or 1-3 halogen atoms, and $R^7$ is hydrogen or methyl, in which cases the nitrogen atom carries a positive charge, or $R^7$ is absent; $R^8$ is hydrogen or a group as defined for $R^3$ and n is 1 or 2;

or $R^4$ and $R^5$ may be joined to form, with the nitrogen, 5 or 6 membered heterocyclic ring, optionally containing an oxygen atom; and $Z^1$, $Z^2$ and $Z^3$ are the same or different and represent hydrogen, a $C_1$-$C_{12}$ straight or branched chain alkyl group, a $C_3$-$C_{12}$ straight or branched chain alkenyl group, a $C_3$-$C_{12}$ straight or branched chain alkynyl group, a $C_4$-$C_{12}$ cycloalkyl group, a phenyl or naphthyl group which may be substituted by a $C_1$-$C_4$ straight or branched chain alkyl group, a $C_1$-$C_4$ alkoxy group, amino, methylamino, halogen or nitro, or a $C_7$-$C_{12}$ aralkyl group.

or $Z^2$ and $Z^3$ together with the nitrogen atom to which they are attached form a saturated or unsaturated 3-7 membered ring system which may optionally contain another hetero atom, and the ring system is optionally substituted by a $C_1$-$C_4$ straight or branched chain alkyl group, a $C_1$-$C_4$ alkoxy group, amino, methylamino, a $C_1$-$C_4$ aminoalkyl group, halogen or nitro;

or $Z^1$ and $Z^2$ and $Z^3$ together with the nitrogen atom to which they are attached form an 8-12 membered bicyclic ring optionally containing another hetero atom, or $Z^1$ is a group of the formula

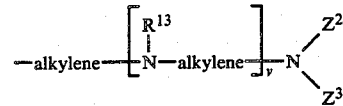

wherein alkylene is a group containing 2 to 12 carbon atoms, v is 0 or an integer from 1 to 5, $R^{13}$ is hydrogen or $C_1$-$C_{16}$ straight or branched chain alkyl group, and $Z^2$ and $Z^3$ are as defined above;

or $Z^1$ is a group of the formula

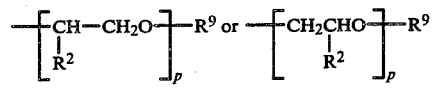

in which $R^2$ is as defined above, $R^9$ is a $C_1$-$C_{12}$ alkyl group and p is an integer from 1-10, preferably from 1-4;

or $Z^3$ is a group of the formula IIa

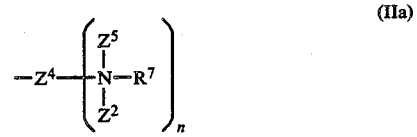

wherein $Z^4$ is an alkylene group of 2-12 carbon atoms, a phenylene group, a xylylene group, a diphenyl methane group or is a group of the formula

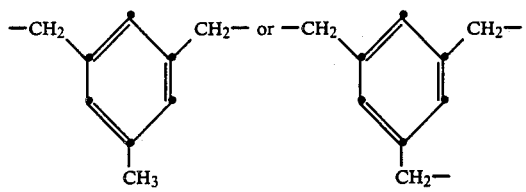

in which aromatic rings in a group $Z^4$ may be substituted by an alkyl group of 1-2 carbon atoms, hydroxyl and/or 1-3 halogen atoms, and $R^7$ is a hydrogen or methyl, in which cases the nitrogen atom carries a positive charge, or $R^7$ is absent; $Z^5$ is hydrogen or a group as defined for $Z^1$ and n is 1 or 2; or $Z^2$ may be joined to form, with the nitrogen, a 3 to 7 membered heterocyclic ring, optionally containing another hetero atom.

* * * * *

UNITED STATES PATENT AND TRADEMARK OFFICE
CERTIFICATE OF CORRECTION

PATENT NO. : 4,656,200

DATED : April 7, 1987

INVENTOR(S) : BRIAN GEORGE CLUBLEY ET AL.

It is certified that error appears in the above-identified patent and that said Letters Patent is hereby corrected as shown below:

Column 22, in the table appearing between lines 43 and 51, correct the two left hand vertical columns to read as follows:

| Example | Number |
|---------|--------|
| -       | None   |
| 70      | 4      |
| 71      | 5      |
| 72      | 13     |
| 73      | 17     |

Signed and Sealed this

Sixteenth Day of February, 1988

Attest:

DONALD J. QUIGG

Attesting Officer

Commissioner of Patents and Trademarks